(12) United States Patent
Smith

(10) Patent No.: US 7,579,315 B2
(45) Date of Patent: Aug. 25, 2009

(54) CASEIN PEPTIDES FOR ALLEVIATING OR PREVENTING AGING OF SKIN

(75) Inventor: John Arthur Smith, Liverpool (GB)

(73) Assignee: Pepsyn Ltd., Liverpool (GB)

( * ) Notice: Subject to any disclaimer, the term of this patent is extended or adjusted under 35 U.S.C. 154(b) by 199 days.

(21) Appl. No.: 10/312,698

(22) PCT Filed: Jun. 13, 2001

(86) PCT No.: PCT/GB01/02601

§ 371 (c)(1), (2), (4) Date: Jun. 18, 2003

(87) PCT Pub. No.: WO02/02133

PCT Pub. Date: Jan. 10, 2002

(65) Prior Publication Data

US 2004/0014653 A1    Jan. 22, 2004

(30) Foreign Application Priority Data

Jun. 30, 2000   (GB) .................... 0016189.3

(51) Int. Cl.
*A61K 38/08* (2006.01)
*A61K 38/10* (2006.01)
*A61K 38/17* (2006.01)

(52) U.S. Cl. ............... 514/12; 514/13; 514/14; 514/15; 514/21

(58) Field of Classification Search ............ None
See application file for complete search history.

(56) References Cited

U.S. PATENT DOCUMENTS

| 3,558,770 | A | * | 1/1971 | Gordon et al. ........... 514/21 |
| 5,284,827 | A | * | 2/1994 | Maione et al. .......... 514/12 |
| 5,965,536 | A | * | 10/1999 | Cohen et al. ........... 514/17 |
| 6,506,732 | B1 | * | 1/2003 | Amiot ................ 514/17 |

FOREIGN PATENT DOCUMENTS

| JP | 3255095 | 11/1991 |
| JP | 6211689 | 8/1994 |
| WO | WO 92/15279 | 9/1992 |
| WO | WO 97/16460 | 3/1997 |

OTHER PUBLICATIONS

Derwent Abstract of WO 92/15279 (Sep. 17, 1992).*
Liu et al., "A Growth Factor Activity in Bovine Milk", Biochemical Society Transactions, Colchester, Essex, GB, vol. 24, No. 3, p. 342S, (1996).
Yokyama et al., 1992, Peptide Inhibitors for Angiotensin I-Converting Enzyme from Thermolysin Digest of Dried Bonito, *Biosci. Biotech. Biochem.*, 56(10), 1541-1545.
Matsui et al., 2002, Absorportion of Val-Tyr with in Vitro Angiotensin I-Converting Enzyme Inhibitory Activity into the Circulating Blood System of Mild Hypertensive Subjects, *Biol. Pharm. Bull.*, 25(9) 1228-1230.

* cited by examiner

*Primary Examiner*—Jeffrey E Russel
(74) *Attorney, Agent, or Firm*—Gavrilovich Dodd & Lindsey LLP; Joseph R. Baker, Jr.

(57) ABSTRACT

Provided is use of a peptide, or a derivative of a peptide, in the manufacture of a medicament effective in alleviating or preventing periodontal disease, wherein the peptide comprises an amino acid sequence present in an α-S2 casein precursor, said sequence comprising 3 or more amino acids, and not comprising at its N-terminus the N-terminal amino acids of the full α-S2 casein precursor. The peptide may alternatively be any peptide having an α-S2 casein fragment activity. Further provided is use of a peptide, or a derivative of a peptide, in the manufacture of a medicament effective in alleviating or preventing an effect of aging in skin, wherein the peptide comprises an amino acid sequence present in a n α-S2 casein precursor, said sequence comprising 3 or more amino acids, and not comprising at its N-terminus the N-terminal amino acid of the full α-S2 casein precursor. The peptide may alternatively be any peptide having an α-S2 casein fragment activity.

3 Claims, 1 Drawing Sheet

Typical CM52 run

Typical Butyl Sepharose run

SEQUENCE LISTING

<160> NUMBER OF SEQ ID NOS: 14

<210> SEQ ID NO 1
<211> LENGTH: 222
<212> TYPE: PRT
<213> ORGANISM: Bos taurus

<400> SEQUENCE: 1

Met Lys Phe Phe Ile Phe Thr Cys Leu Leu Ala Val Ala Leu Ala Lys
1               5                   10                  15

Asn Thr Met Glu His Val Ser Ser Glu Glu Ser Ile Ile Ser Gln
            20                  25                  30

Glu Thr Tyr Lys Gln Glu Lys Asn Met Ala Ile Asn Pro Ser Lys Glu
        35                  40                  45

Asn Leu Cys Ser Thr Phe Cys Lys Glu Val Val Arg Asn Ala Asn Glu
    50                  55                  60

Glu Glu Tyr Ser Ile Gly Ser Ser Ser Glu Glu Ser Ala Glu Val Ala
65                  70                  75                  80

Thr Glu Glu Val Lys Ile Thr Val Asp Asp Lys His Tyr Gln Lys Ala
                85                  90                  95

Leu Asn Glu Ile Asn Gln Phe Tyr Gln Lys Phe Pro Gln Tyr Leu Gln
            100                 105                 110

Tyr Leu Tyr Gln Gly Pro Ile Val Leu Asn Pro Trp Asp Gln Val Lys
        115                 120                 125

Arg Asn Ala Val Pro Ile Thr Pro Thr Leu Asn Arg Glu Gln Leu Ser
    130                 135                 140

Thr Ser Glu Glu Asn Ser Lys Lys Thr Val Asp Met Glu Ser Thr Glu
145                 150                 155                 160

Val Phe Thr Lys Lys Thr Lys Leu Thr Glu Glu Glu Lys Asn Arg Leu
                165                 170                 175

Asn Phe Leu Lys Lys Ile Ser Gln Arg Tyr Gln Lys Phe Ala Leu Pro
            180                 185                 190

Gln Tyr Leu Lys Thr Val Tyr Gln His Gln Lys Ala Met Lys Pro Trp
        195                 200                 205

Ile Gln Pro Lys Thr Lys Val Ile Pro Tyr Val Arg Tyr Leu
    210                 215                 220

<210> SEQ ID NO 2
<211> LENGTH: 9
<212> TYPE: PRT
<213> ORGANISM: Bos taurus

<400> SEQUENCE: 2

Lys Val Ile Pro Tyr Val Arg Tyr Leu
1               5

<210> SEQ ID NO 3
<211> LENGTH: 10
<212> TYPE: PRT
<213> ORGANISM: Bos taurus

<400> SEQUENCE: 3

Thr Lys Val Ile Pro Tyr Val Arg Tyr Leu
1               5                   10

<210> SEQ ID NO 4
<211> LENGTH: 11

```
<212> TYPE: PRT
<213> ORGANISM: Bos taurus

<400> SEQUENCE: 4

Lys Thr Lys Val Ile Pro Tyr Val Arg Tyr Leu
1               5                   10

<210> SEQ ID NO 5
<211> LENGTH: 12
<212> TYPE: PRT
<213> ORGANISM: Bos taurus

<400> SEQUENCE: 5

Pro Lys Thr Lys Val Ile Pro Tyr Val Arg Tyr Leu
1               5                   10

<210> SEQ ID NO 6
<211> LENGTH: 13
<212> TYPE: PRT
<213> ORGANISM: Bos taurus

<400> SEQUENCE: 6

Gln Pro Lys Thr Lys Val Ile Pro Tyr Val Arg Tyr Leu
1               5                   10

<210> SEQ ID NO 7
<211> LENGTH: 19
<212> TYPE: PRT
<213> ORGANISM: Bos taurus

<400> SEQUENCE: 7

Ala Met Lys Pro Trp Ile Gln Pro Lys Thr Lys Val Ile Pro Tyr Val
1               5                   10                  15

Arg Tyr Leu

<210> SEQ ID NO 8
<211> LENGTH: 31
<212> TYPE: PRT
<213> ORGANISM: Bos taurus

<400> SEQUENCE: 8

Pro Gln Tyr Leu Lys Thr Val Tyr Gln His Gln Lys Ala Met Lys Pro
1               5                   10                  15

Trp Ile Gln Pro Lys Thr Lys Val Ile Pro Tyr Val Arg Tyr Leu
                20                  25                  30

<210> SEQ ID NO 9
<211> LENGTH: 223
<212> TYPE: PRT
<213> ORGANISM: Capra hircus

<400> SEQUENCE: 9

Met Lys Phe Phe Ile Phe Thr Cys Leu Leu Ala Val Ala Leu Ala Lys
1               5                   10                  15

His Lys Met Glu His Val Ser Ser Ser Glu Glu Pro Ile Asn Ile Phe
                20                  25                  30

Gln Glu Ile Tyr Lys Gln Glu Lys Asn Met Ala Ile His Pro Arg Lys
        35                  40                  45

Glu Lys Leu Cys Thr Thr Ser Cys Glu Glu Val Val Arg Asn Ala Asn
    50                  55                  60

Glu Glu Glu Tyr Ser Ile Arg Ser Ser Glu Glu Ser Ala Glu Val
65                  70                  75                  80
```

```
Ala Pro Glu Glu Ile Lys Ile Thr Val Asp Asp Lys His Tyr Gln Lys
                85                  90                  95

Ala Leu Asn Glu Ile Asn Gln Phe Tyr Gln Lys Phe Pro Gln Tyr Leu
            100                 105                 110

Gln Tyr Pro Tyr Gln Gly Pro Ile Val Leu Asn Pro Trp Asp Gln Val
        115                 120                 125

Lys Arg Asn Ala Gly Pro Phe Thr Pro Thr Val Asn Arg Glu Gln Leu
    130                 135                 140

Ser Thr Ser Glu Glu Asn Ser Lys Lys Thr Ile Asp Met Glu Ser Thr
145                 150                 155                 160

Glu Val Phe Thr Lys Lys Thr Lys Leu Thr Glu Glu Glu Lys Asn Arg
                165                 170                 175

Leu Asn Phe Leu Lys Lys Ile Ser Gln Tyr Tyr Gln Lys Phe Ala Trp
            180                 185                 190

Pro Gln Tyr Leu Lys Thr Val Asp Gln His Gln Lys Ala Met Lys Pro
        195                 200                 205

Trp Thr Gln Pro Lys Thr Asn Ala Ile Pro Tyr Val Arg Tyr Leu
    210                 215                 220

<210> SEQ ID NO 10
<211> LENGTH: 223
<212> TYPE: PRT
<213> ORGANISM: Capra hircus

<400> SEQUENCE: 10

Met Lys Phe Phe Ile Phe Thr Cys Leu Leu Ala Val Ala Leu Ala Lys
1               5                   10                  15

His Lys Met Glu His Val Ser Ser Ser Glu Glu Pro Ile Asn Ile Phe
            20                  25                  30

Gln Glu Ile Tyr Lys Gln Glu Lys Asn Met Ala Ile His Pro Arg Lys
        35                  40                  45

Glu Lys Leu Cys Thr Thr Ser Cys Glu Glu Val Val Arg Asn Ala Asn
    50                  55                  60

Glu Glu Glu Tyr Ser Ile Arg Ser Ser Ser Glu Ser Ala Lys Val
65                  70                  75                  80

Ala Pro Glu Glu Ile Lys Ile Thr Val Asp Asp Lys His Tyr Gln Lys
                85                  90                  95

Ala Leu Asn Glu Ile Asn Gln Phe Tyr Gln Lys Phe Pro Gln Tyr Leu
            100                 105                 110

Gln Tyr Pro Tyr Gln Gly Pro Ile Val Leu Asn Pro Trp Asp Gln Val
        115                 120                 125

Lys Arg Asn Ala Gly Pro Phe Thr Pro Thr Val Asn Arg Glu Gln Leu
    130                 135                 140

Ser Thr Ser Glu Glu Asn Ser Lys Lys Thr Ile Asp Met Glu Ser Thr
145                 150                 155                 160

Glu Val Phe Thr Lys Lys Thr Lys Leu Thr Glu Glu Glu Lys Asn Arg
                165                 170                 175

Leu Asn Phe Leu Lys Lys Ile Ser Gln Tyr Tyr Gln Lys Phe Ala Trp
            180                 185                 190

Pro Gln Tyr Leu Lys Thr Val Asp Gln His Gln Lys Ala Met Lys Pro
        195                 200                 205

Trp Thr Gln Pro Lys Thr Asn Ala Ile Pro Tyr Val Arg Tyr Leu
    210                 215                 220
```

<210> SEQ ID NO 11
<211> LENGTH: 222
<212> TYPE: PRT
<213> ORGANISM: Capra hircus

<400> SEQUENCE: 11

Met Lys Phe Phe Ile Phe Thr Cys Leu Leu Ala Val Ala Leu Ala Lys
1               5                   10                  15

His Lys Met Glu His Val Ser Ser Ser Glu Glu Pro Ile Asn Ile Phe
            20                  25                  30

Gln Glu Ile Tyr Lys Gln Glu Lys Asn Met Ala Ile His Pro Arg Lys
        35                  40                  45

Glu Lys Leu Cys Thr Thr Ser Cys Glu Glu Trp Arg Asn Ala Asn Glu
50                  55                  60

Glu Glu Tyr Ser Ile Arg Ser Ser Ser Glu Glu Ser Ala Glu Val Ala
65                  70                  75                  80

Pro Glu Glu Ile Lys Ile Thr Val Asp Asp Lys His Tyr Gln Lys Ala
                85                  90                  95

Leu Asn Glu Ile Asn Gln Phe Tyr Gln Lys Phe Pro Gln Tyr Leu Gln
            100                 105                 110

Tyr Pro Tyr Gln Gly Pro Ile Val Leu Asn Pro Trp Asp Gln Val Lys
        115                 120                 125

Arg Asn Ala Gly Pro Phe Thr Pro Thr Val Asn Arg Glu Gln Leu Ser
130                 135                 140

Thr Ser Glu Glu Asn Ser Lys Lys Thr Ile Asp Met Glu Ser Thr Glu
145                 150                 155                 160

Val Phe Thr Lys Lys Thr Lys Leu Thr Glu Glu Lys Asn Arg Leu
                165                 170                 175

Asn Phe Leu Lys Ile Ile Ser Gln Tyr Tyr Gln Lys Phe Ala Trp Pro
            180                 185                 190

Gln Tyr Leu Lys Thr Val Asp Gln His Gln Lys Ala Met Lys Pro Trp
        195                 200                 205

Thr Gln Pro Lys Thr Asn Ala Ile Pro Tyr Val Arg Tyr Leu
210                 215                 220

<210> SEQ ID NO 12
<211> LENGTH: 178
<212> TYPE: PRT
<213> ORGANISM: Oryctolagus cuniculus

<400> SEQUENCE: 12

Met Lys Phe Phe Ile Phe Thr Cys Leu Leu Ala Val Ala Leu Ala Lys
1               5                   10                  15

Pro Lys Ile Glu Gln Ser Ser Glu Glu Thr Ile Ala Val Ser Gln Glu
            20                  25                  30

Val Ser Pro Asn Leu Glu Asn Ile Cys Ser Thr Ala Cys Glu Glu Pro
        35                  40                  45

Ile Lys Asn Ile Asn Glu Val Glu Tyr Val Glu Val Pro Thr Glu Ile
50                  55                  60

Lys Asp Gln Glu Phe Tyr Gln Lys Val Asn Leu Gln Tyr Leu Gln
65                  70                  75                  80

Ala Leu Tyr Gln Tyr Pro Thr Val Met Asp Pro Trp Thr Arg Ala Glu
                85                  90                  95

Thr Lys Ala Ile Pro Phe Ile Arg Thr Met Gln Tyr Lys Gln Glu Lys
            100                 105                 110

Asp Ala Thr Lys His Thr Ser Gln Lys Thr Glu Leu Thr Glu Glu Glu

```
                115                 120                 125
Lys Ala Phe Leu Lys Tyr Leu Asp Glu Met Lys Gln Tyr Tyr Gln Lys
    130                 135                 140

Phe Val Phe Pro Gln Tyr Leu Lys Asn Ala His His Phe Gln Lys Thr
145                 150                 155                 160

Met Asn Pro Trp Asn His Val Lys Thr Ile Ile Tyr Gln Val Pro Thr
                165                 170                 175

Ser Leu

<210> SEQ ID NO 13
<211> LENGTH: 220
<212> TYPE: PRT
<213> ORGANISM: Ovis aries

<400> SEQUENCE: 13

Met Lys Phe Phe Ile Phe Thr Cys Leu Leu Ala Val Ala Leu Ala Lys
1               5                   10                  15

His His Val Ser Ser Glu Glu Pro Ile Asn Ile Ser Gln Glu Ile
                20                  25                  30

Tyr Lys Gln Glu Lys Asn Met Ala Ile His Pro Arg Lys Glu Lys Leu
            35                  40                  45

Cys Thr Thr Ser Cys Glu Glu Val Val Arg Asn Ala Asp Glu Glu
        50                  55                  60

Tyr Ser Ile Arg Ser Ser Glu Glu Ser Ala Glu Val Ala Pro Glu
65                  70                  75                  80

Glu Val Lys Ile Thr Val Asp Asp Lys His Tyr Gln Lys Ala Leu Asn
                85                  90                  95

Glu Ile Asn Gln Phe Tyr Gln Lys Phe Pro Gln Tyr Leu Gln Tyr Leu
            100                 105                 110

Tyr Gln Gly Pro Ile Val Leu Asn Pro Trp Asp Gln Val Lys Arg Asn
        115                 120                 125

Ala Gly Pro Phe Thr Pro Thr Val Asn Arg Glu Gln Leu Ser Thr Ser
    130                 135                 140

Glu Glu Asn Ser Lys Lys Thr Ile Asp Met Glu Ser Thr Glu Val Phe
145                 150                 155                 160

Thr Lys Lys Thr Lys Leu Thr Glu Glu Lys Asn Arg Leu Asn Phe
                165                 170                 175

Leu Lys Lys Ile Ser Gln Tyr Tyr Gln Lys Phe Ala Trp Pro Gln Tyr
            180                 185                 190

Leu Lys Thr Val Asp Gln His Gln Lys Ala Met Lys Pro Trp Thr Gln
        195                 200                 205

Pro Lys Thr Asn Ala Ile Pro Tyr Val Arg Tyr Leu
    210                 215                 220

<210> SEQ ID NO 14
<211> LENGTH: 234
<212> TYPE: PRT
<213> ORGANISM: Sus scrofa

<400> SEQUENCE: 14

Met Lys Phe Phe Ile Phe Thr Cys Leu Leu Ala Val Ala Phe Ala Lys
1               5                   10                  15

His Glu Met Glu His Val Ser Ser Glu Glu Ser Ile Asn Ile Ser
                20                  25                  30

Gln Glu Lys Tyr Lys Gln Glu Lys Asn Val Ile Asn His Pro Ser Lys
            35                  40                  45
```

-continued

```
Glu Asp Ile Cys Ala Thr Ser Cys Glu Glu Ala Val Arg Asn Ile Lys
     50                  55                  60
Glu Val Gly Tyr Ala Ser Ser Ser Ser Glu Gln Ser Val Asp Ile
65                   70                  75                  80
Pro Ala Glu Asn Val Lys Val Thr Val Glu Asp Lys His Tyr Leu Lys
                 85                  90                  95
Gln Leu Glu Lys Ile Ser Gln Phe Tyr Gln Lys Phe Pro Gln Tyr Leu
                100                 105                 110
Gln Ala Leu Tyr Gln Ala Gln Ile Val Met Asn Pro Trp Asp Gln Thr
            115                 120                 125
Lys Thr Ser Ala Tyr Pro Phe Ile Pro Thr Val Ile Gln Ser Gly Glu
        130                 135                 140
Glu Leu Ser Thr Ser Glu Glu Pro Val Ser Ser Ser Gln Glu Glu Asn
145                 150                 155                 160
Thr Lys Thr Val Asp Glu Ser Met Glu Glu Phe Thr Lys Lys Thr Glu
                165                 170                 175
Leu Thr Glu Glu Glu Lys Asn Arg Ile Lys Phe Leu Asn Lys Ile Lys
            180                 185                 190
Gln Tyr Tyr Gln Lys Phe Thr Trp Pro Gln Tyr Ile Lys Thr Val His
        195                 200                 205
Gln Lys Gln Lys Ala Met Lys Pro Trp Asn His Ile Lys Thr Asn Ser
    210                 215                 220
Tyr Gln Ile Ile Pro Asn Leu Arg Tyr Phe
225                 230
```

CASEIN PEPTIDES FOR ALLEVIATING OR PREVENTING AGING OF SKIN

Figure 1:
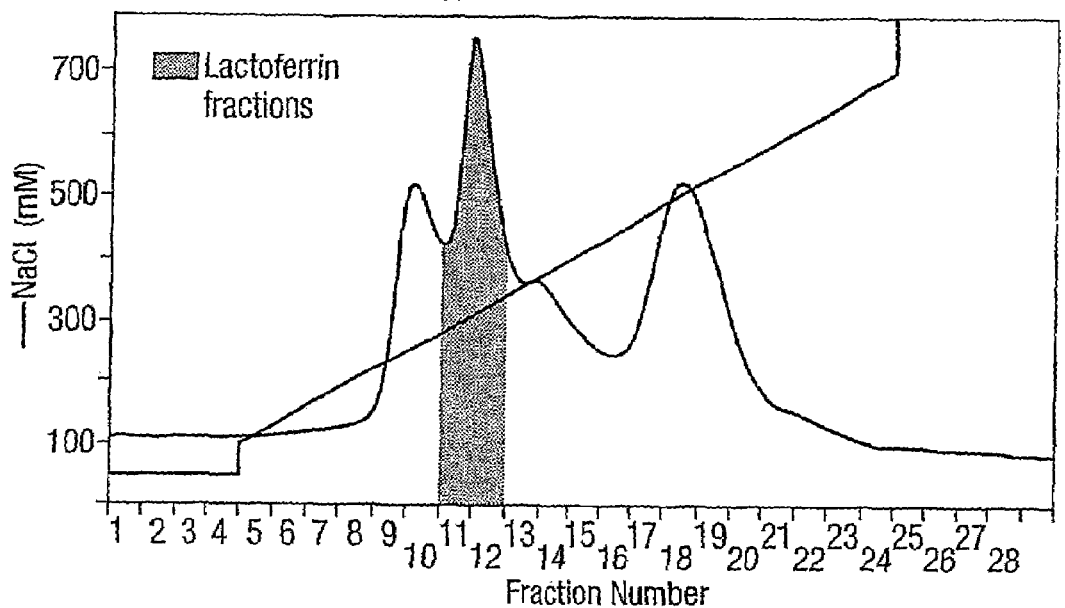

This application is the National Phase of International Application PCT/GB01/02601 filed Jun. 13, 2001 which designated the U.S. and that International Application was not published under PCT Article 21(2) in English.

The present invention relates to a protein, a peptide (generally a polypeptide), a peptide derivative, or peptide fragment which can be used to alleviate or prevent an effect of aging, particularly an effect of aging in ski. This may be in a method of treatment or a cosmetic method. The invention also relates to the same peptides, polypeptides, peptide derivatives or peptide fragments which can be used as a prophylactic or treatment for periodontal diseases (gum diseases). This may be in a medical method of treatment if desired. In particular the invention relates to use of a peptide which comprises an amino acid sequence from an α-S2 casein precursor.

For many years it has been known that, in addition to its nutritional content, milk contains growth promoting activity for cells. In this connection, epidermal growth factor (EGF) has been identified in human (Shing and Klagsbrun, 1984; Petrides, 1985), rat (Raaberg et al., 1990), swine (Tan et aL, 1990) and goat (Brown and Blalceley, 1983) milk.

The EGF present in rat milk has been shown to be significant for the normal development of rat pups (Oka et al., 1983). EGF has not, however, been found in bovine milk (Read 1985). Instead, insulin-like growth factor (IGF) I and II (Francis et al., 1986) and bovine colostrum growth factor (BCGF), which is structurally related to Platelet-derived Growth Factor (PDGF) (Shing and Klagsbrun, 1984; Brown and Blakeley, 1994), have been identified in bovine milk.

In published International Application WO 97/16460 it is disclosed that bovine milk contains growth promoting activity for a rat mammary fibroblast cell line (Rama 27), which is not significantly stimulated by IFG or PDGF. In this application peptide sequences are identified which elicit this growth promoting activity. These sequences are identified as sequences that are substantially identical to the C-terminal end of bovine α-S2 casein precursor. The application indicates that these peptides or salts thereof may be used for the manufacture of medicaments or foodstuffs for promoting growth.

Published European Patent Application EP 0 457 565 discloses milk protein hydrolysate and compositions for use in hair and skin treatment. The proteins in the hydrolysate are not specifically defined and have molecular weights of less than 1000 daltons. These are thus very small hydrolysis products from a wide variety of proteins present in milk.

Published PCT Applications WO 92/00994, WO 95/29933 and WO 96/34614 disclose extracts from milk which may be used as growth promoting agents and agents for treating alimentary tract damage. The milk product extract may be from human or animal milk and includes cheese whey extracts and skim-milk extracts. The documents imply that IGF I or II are active ingredients giving the products their utility, and do not indicate that the products should comprise any specific protein.

In addition, topical applications, such as creams, have been marketed that claim anti-aging efficacy for added Epidermal Growth Factor (EGF) (Estee Lauder, advertised in Elle, 1999) and for 'whey proteins' (Estee Lauder's 'Diminish' in Martha Stewart's Living, February 2000). However, this efficacy has not been shown to be especially high.

It is an object of the present invention to solve the problems associated with the prior art. In particular, it is an object of the present invention to provide an agent capable of alleviating or preventing the effects of aging in skin. It is also an object of the invention to provide an agent capable of treating or preventing periodontal disease. Surprisingly, the inventors have found that an α-S2 casein precursor and related species, such as those disclosed as growth promoters in WO 97/16460, are extremely useful in alleviating and preventing the effects of aging in skin, and in treating periodontal disease. The α-S2 casein precursor and precursor fragments and derivatives used in the present invention are superior to known anti-aging products and products used for treating gum disease, and in particular to the agents disclosed in the above prior art.

Accordingly, the present invention provides use of a peptide, or a derivative of a peptide, in the manufacture of a medicament effective in alleviating or preventing periodontal disease, wherein the peptide comprises an amino acid sequence present in an α-S2 casein precursor, said sequence comprising 3 or more amino acids, and not comprising at its N-terminus the N-terminal amino acid of the fall α-S2 casein precursor. The invention also provides use of a peptide, or a derivative of a peptide, in the manufacture of a medicament effective in alleviating or preventing an effect of aging in skin, wherein the peptide comprises an amino acid sequence present in an α-S2 casein precursor, said sequence comprising 3 or more amino acids, and not comprising at its N-terminus the N-terminal amino acid of the full α-S2 casein precursor.

The above-defined uses of the present invention include use. of the peptide, or its derivative, either in a pure form, or in a partially purified form, such as that obtainable by isolation of the peptide from a natural source. Thus, the present use may extend to employment of the peptide in its natural unpurified form, such as using a natural substance that comprises the peptide or its derivative, or may involve use of the peptide or its derivative in any level of purification, including entirely (100%) pure. The peptide may also be from a proteolytic digest or a non-natural source, such as a synthetic peptide. In the context of this invention, the term peptide is intended to include proteins, polypeptides and peptide fragments.

The present invention also provides a cosmetic method for alleviating or preventing an effect of aging in skin, which method comprises treating a subject with a polypeptide, or a derivative of a polypeptide, wherein the polypeptide comprises an amino acid sequence present in an α-S2 casein precursor, said sequence comprising 3 or more amino acids, and not comprising the N-terminus of the full α-S2 casein precursor.

To reiterate, the present inventors have surprisingly found that a peptide comprising an amino acid sequence from an α-S2 casein precursor, and in particular a fragment of such a peptide, has a very beneficial effect upon the skin, preventing and alleviating many effects of aging, and treating and preventing periodontal disease. The effect of these particular agents is superior to the effect of prior art agents. By fragments, in the context of the present invention it is meant any part of a sequence from a protein, polypeptide or peptide that is not the fall sequence.

Figure 2:
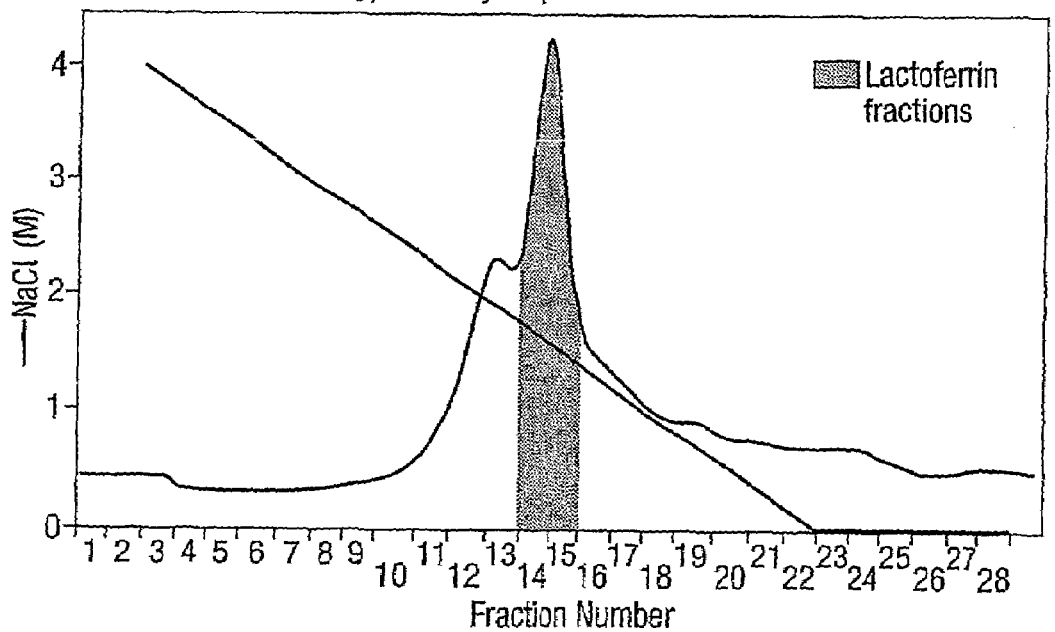

The invention will be further described by way of example only with reference to the following drawings and specific embodiments, in which:

FIG. 1 shows the result of a cation exchange column chromatography experiments are carried out on a dialysed cheese whey salt-cut; and FIG. 2 shows the results of a hydrophobic interaction column chromatography experiment performed on active fractions from cation exchange chromatogaphy.

In the context of the present invention, the effect of aging may be any effect of aging. Thus the effect may be sagging of the skin, wrinkling of the skin or slow regeneration of damaged areas of skin. However, the effect is most preferably wrinkling of the skin. The periodontal disease is a disease of the gums. In the context of the present invention, this may be a gum disease arising for any reason, including infection of the teeth or gums as well as lack of cleaning (brushing or flossing) of the teeth or gums.

The polypeptide and polypeptide fragments used in the present invention may have either an alleviating effect, or a preventative effect, or both. Thus, they may have a prophylactic effect and/or may reduce the effects of gum disease or of aging, or provide protection against the onset of gum disease or may increase the youthful appearance of the skin.

Whilst the whole α-S2 casein precursor shows no significant efficacy against the effects of aging or gum disease, fragments of such proteins, such as polypeptides derived from the C-terminal end of α-S2 caseins, do have these effects. For example, the efficacy against gum disease and effects of aging is present in peptides which are derived from the C-terminal end of α-S2 casein precursors and have 3 or more amino acids, but do not comprise the N-terminal amino acid of the full α-S2 casein molecule. Thus, the casein-derived peptides and fragments used in the present invention generally comprise 3 or more amino acids and do not comprise the N-terminus of the fall casein protein. In the context of the present invention, the peptide not comprising the N-terminal amino acid means that the peptide does not comprise the N-terminal end (N-terminus) of the protein itself. In some embodiments this can mean that the peptide does not comprise a number of amino acids up to and including the N-terminus. Preferably the peptides do comprise the C-terminus of the full protein.

Thus, the number of amino acids in the peptide or fragment used the present invention is not especially limited, provided that it has 3 or more amino acids, but does not comprise the N-terminal end of the full casein. However, it is preferred that the number of amino acids in the peptide is from 3-50, 4-50, 5-50, 6-50, or 7-50. Advantageously, the number of amino acids may be from 8-50 and more preferably from 9-50 or 10-50. It is particularly preferred that the upper limit on the amino acids in all these cases is 35 and most preferably 31. The most preferred number of amino acids is from 9-31.

Thus, the peptide may preferably comprise the last 3-50, 3-35 or 3-31 amino acids of the C-terminal end of the α-S2 casein precursor (including the C-terminus) and may even be as short as the last 3-10, 3-9, 3-8 or 3-7 or even just the last 3 amino acids of the C-terminal end of the α-S2 casein.

The bovine α-S2 casein precursor used in the present invention has the following amino acid sequence:

```
[CAS2_BOVIN] ALPHA-S2 CASEIN PRECURSOR SEQUENCE:
                                        (SEQ ID NO: 1)
MKFFIFTCLL AVALAKNTME HVSSSEESII SQETYKQEKN

MAINPSKENL CSTFCKEVVR NANEEEYSIG SSSEESAEVA

TEEVKITVDD KHYQKALNEI NQFYQKFPQY LQYLYQGPIV

LNPWDQVKRN AVPITPTLNR EQLSTSEENS KKTVDMESTE

VFTKKTKLTE EEKNRLNFLK KISQRYQKFA LPQYLKTVYQ

HQKAMKPWIQ PKTKVIPYVR YL
```

In three letter codes this translates to:

```
                                        (SEQ ID NO: 1)
Met Lys Phe Phe Ile Phe Thr Cys Leu Leu

Ala Val Ala Leu Ala Lys Asn Thr Met Glu

His Val Ser Ser Ser Glu Glu Ser Ile Ile

Ser Gln Glu Thr Tyr Lys Gln Glu Lys Asn
```

```
-continued
Met Ala Ile Asn Pro Ser Lys Glu Asn Leu

Cys Ser Thr Phe Cys Lys Glu Val Val Arg

Asn Ala Asn Glu Glu Glu Tyr Ser Ile Gly

Ser Ser Ser Glu Glu Ser Ala Glu Val Ala

Thr Glu Glu Val Lys Ile Thr Val Asp Asp

Lys His Tyr Gln Lys Ala Leu Asn Glu Ile

Asa Gln Phe Tyr Gln Lys Phe Pro Gln Tyr

Leu Gln Tyr Leu Tyr Gln Gly Pro Ile Val

Leu Asn Pro Trp Asp Gln Val Lys Arg Asn

Ala Val Pro Ile Thr Pro Thr Leu Asn Arg

Glu Gln Leu Ser Thr Ser Glu Glu Asn Ser

Lys Lys Thr Val Asp Met Glu Ser Thr Glu

Val Phe Thr Lys Lys Thr Lys Leu Thr Glu

Glu Glu Lys Asn Arg Leu Asn Phe Leu Lys

Lys Ile Ser Gln Arg Tyr Gln Lys Phe Ala

Leu Pro Gln Tyr Leu Lys Thr Val Tyr Gln

His Gln Lys Ala Met Lys Pro Trp Ile Gln

Pro Lys Thr Lys Val Ile Pro Tyr Val Arg

Tyr Leu
```

It is preferred in the present invention that the peptide comprises an amino acid sequence selected from the following sequences:

```
                                        (SEQ ID NO: 2)
Lys Val Ile Pro Tyr Val Arg Tyr Leu (SEQ ID NO: 3)
Thr Lys Val Ile Pro Tyr Val Arg Tyr Leu (SEQ ID NO: 4)
Lys Thr Lys Val Ile Pro Tyr Val Arg Tyr Leu (SEQ ID NO: 5)
Pro Lys Thr Lys Val Ile Pro Tyr Val Arg Tyr
Leu (SEQ ID NO: 6)
Gln Pro Lys Thr Lys Val Ile Pro Tyr Val Arg
Tyr Leu (SEQ ID NO: 7)
Ala Met Lys Pro Trp Ile Gln Pro Lys Thr Lys
Val Ile Pro Tyr Val Arg Tyr Leu; and (SEQ ID NO: 8)
Pro Gln Tyr Leu Lys Thr Val Tyr Gln His Gln
Lys Ala Met Lys Pro Trp Ile Gln Pro Lys Thr Lys
Val Ile Pro Tyr Val Arg Tyr Leu.
```

These sequences all comprise the last 9 amino acids of the C-terminal end of the bovine α-S2 casein precursor. The present inventors have found that peptide sequences incorporating this C-terminal sequence, Lys Val Ile Pro Tyr Val Arg Tyr Leu (SEQ ID NO:2), show particularly marked anti aging activity. Thus in a particularly preferred aspect of the present invention the polypeptide comprises a bovine α-S2 casein fragment comprising the sequence Lys Val Ile Pro Tyr Val Arg Tyr Leu (SEQ ID NO:2). Other particularly preferred sequences referred to above include the last 10, 11, 12 and 13 amino acids of the C-terminal end of the bovine α-S2 casein precursor. These amino acids are also the same as the last 7 amino acids of the goat, rabbit and sheep α-S2 casein precursors, confirming the degree of similarity between these proteins, particularly at their C-termini.

As highlighted above, there is a high degree of homology between the C-terminal end sequence of α-S2 casein precursors of bovine, goat, sheep, rabbit and pig origin. It is apparent from the sequences of these caseins that the C-terminal sequence can vary from species to species, but that there are important similarities. Accordingly, whilst bovine α-S2 casein precursor fragments are preferred for use in the present invention, goat, sheep, rabbit and pig α-S2 casein fragments, or similar fragments from other species, may also be employed if desired.

The sequences for α-S2 casein precursors of goat, sheep, rabbit and pig origin are set out below.

```
[CAS2 CAPH1]         α-S2 casein precursor (α-S2-CN)
SEQUENCE:
                                         (SEQ ID NO: 9)
MKFFIFTCLL AVALAKHKME HVSSSEEPIN IFQEIYKQEK

NMAIHPRKEK LCTTSCEEVV RNANEEEYSI RSSSEESAEV

APEEIKITVD DKHYQKALNE INQFYQKFPQ YLQYPYQGPI

VLNPWDQVKR NAGPFTPTVN REQLSTSEEN SKKTIDMEST

EVFTKKTKLT EEEKNRLNFL KKISQYYQKF AWPQYLKTVD

QHQKAMKPWT QPKTNAIPYV RYL 223

>pir|S33881|S33881          α-S2 casein E - goat
SEQUENCE:
                                         (SEQ ID NO: 10)
MKFFIFTCLL AVALAKHKME HVSSSEEPIN IFQEIYKQEK

NMAIHPRKEK LCTTSCEEVV RNANEEEYSI RSSSEESAKV

APEEIKITVD DKHYQKALNE INQFYQKFPQ YLQYPYQGPI

VLNPWDQVKR NAGPFTPTVN REQLSTSEEN SKKTIDMEST

EVFTKKTKLT EEEKNRLNFL KKISQYYQKF AWPQYLKTVD

QHQKAMKPWT QPKTNAIPYV RYL 223

>gp|S74171|S74171_1     α-S2 casein C-capra hircus
SEQUENCE:
                                         (SEQ ID NO: 11)
MKFFIFTCLL AVALAKHKME HVSSSEEPIN IFQEIYKQEK

NMAIHPRKEK LCTTSCEEVV RNANEEEYSI RSSSEESAEV

APEEIKITVD DKHYQKALNE INQFYQKFPQ YLQYPYQGPI

VLNPWDQVKR NAGPFTPTVN REQLSTSEEN SKKTIDMEST

EVFTKKTKLT EEEKNRLNFL KKISQYYQKF AWPQYLKTVD

QHQKAMKPWT QPKTNAIPYV RYL 223

>pir|S39776|S39776          α-S2 casein form b
                                   precursor-rabbit
>gp|X76909|OCPAS2BCS_1   pre-α-S2b casein (AA -15 to
                                                167)
Oryctolagus cuniculus
SEQUENCE
                                         (SEQ ID NO: 12)
MKFFIFTCLL AVALAKPKIE QSSEETIAV SQEVSPNLEN

ICSTACEEPI KNINEVEYVE VPTEIKDQEF YQKVNLLQYL

QALYQYPTVM DPWTRAETKA IPFIRTMQYK QEKDATKHTS

QKTELTEEEK AFLKYLDEMK QYYQKFVFPQ YLKNAHHFQK

TMNPWNHVKT IIYQVPTSL 179

[CAS2_SHEEP]            α-S2 casein precursor-sheep
SEQUENCE:
                                         (SEQ ID NO: 13)
MKFFIFTCLL AVALAKHKME HVSSSEEPIN ISQEIYKQEK

NMAIHPRKEK LCTTSCEEVV RNADEEEYSI RSSSEESAEV

APEEVKITVD DKHYQKALNE INQFYQKFPQ YLQYLYQGPI

VLNPWDQVKR NAGPFTPTVN REQLSTSEEN SKKTIDMEST

EVFTKKTKLT EEEKNRLNFL KKISQYYQKF AWPQYLKTVD

QHQKAMKPWT QPKTNAIPYV RYL 223

[CAS2_PIG]                α-S2 casein precursor-pig
SEQUENCE:
                                         (SEQ ID NO: 14)
MKFFIFTCLL AVAFAKHEME HVSSSEESIN ISQEKYKQEK

NVINHPSKED ICATSCEEAV RNIKEVGYAS SSSSEESVDI

PAENVKVTVE DKHYLKQLEK ISQFYQKFPQ YLQALYQAQI

VMNPWDQTKT SAYPFIPTVI QSGEELSTSE EPVSSSQEEN

TKTVDESME EFTKKTELTE EEKNRIKFLN KIKQYYQKFT

WPQYIKTVHQ KQKAMKPWNH IKTNSYQIIP NLRYF 234
```

In three letter codes, these sequences translate to the following.

```
[CAS2 CAPH1]          αS2 casein precursor (α-S2-CN)
SEQUENCE:
                                         (SEQ ID NO: 9)
Met Lys Phe Ile Phe Phe Thr Cys Leu Leu Ala Val Ala Leu Ala Lys His Lys Met Glu His Val Ser Ser Ser Glu Glu Pro Ile Asn Ile Phe Gln Glu Ile Tyr Lys Gln Glu Lys Asn Met Ala Ile His Pro Arg Lys Glu Lys Leu Cys Thr Thr Ser Cys Glu Glu Val Val Arg Asn Ala Asn Glu Glu Glu Tyr Ser Ile Arg Ser Ser Ser Glu Glu Ser Ala Glu Val Ala Pro Glu Glu Ile Lys Ile Thr Val Asp Asp Lys His Tyr Gln Lys Ala Leu Asn Glu Ile Asn Gln Phe Tyr Gln Lys Phe Pro Gln Tyr Leu Gln Tyr Pro Tyr Gln Gly Pro Ile Val Leu Asn Pro Trp Asp Gln Val Lys Arg Asn Ala Gly Pro Phe Thr Pro Thr Val Asn Arg Glu Gln Leu Ser Thr Ser Glu Glu Asn Ser Lys Lys Thr Ile Asp Met Glu Ser Thr
```

-continued

Glu Val Phe Thr Lys Lys Thr Lys Leu Thr

Glu Glu Glu Lys Asn Arg Leu Asn Phe Leu

Lys Lys Ile Ser Gln Tyr Tyr Gln Lys Phe

Ala Trp Pro Gln Tyr Leu Lys Thr Val Asp

Gln His Gln Lys Ala Met Lys Pro Trp Thr

Gln Pro Lys Thr Asn Ala Ile Pro Tyr Val

Arg Tyr Leu

>pir|S33881|S33881    α-S2 casein E-goat
SEQUENCE:
                              (SEQ ID NO: 10)
Met Lys Phe Phe Ile Phe Thr Cys Leu Leu Ala Val Ala Leu Ala Lys His Lys Met Glu His Val Ser Ser Ser Glu Glu Pro Ile Asn Ile Phe Gln Glu Ile Tyr Lys Gln Glu Lys Asn Met Ala Ile His Pro Arg Lys Glu Lys Leu Cys Thr Thr Ser Cys Glu Glu Val Val Arg Asn Ala Asn Glu Glu Glu Tyr Ser Ile Arg Ser Ser Ser Glu Glu Ser Ala Lys Val Ala Pro Glu Glu Ile Lys Ile Thr Val Asp Asp Lys His Tyr Gln Lys Ala Leu Asn Glu Ile Asn Gln Phe Tyr Gln Lys Phe Pro Gln Tyr Leu Gln Tyr Pro Tyr Gln Gly Pro Ile Val Leu Asn Pro Trp Asp Gln Val Lys Arg Asn Ala Gly Pro Phe Thr Pro Thr Val Asn Arg Glu Gln Leu Ser Thr Ser Glu Glu Asn Ser Lys Lys Thr Ile Asp Met Glu Ser Thr Glu Val Phe Thr Lys Lys Thr Lys Leu Thr Glu Glu Glu Lys Asn Arg Leu Asn Phe Leu Lys Lys Ile Ser Gln Tyr Tyr Gln Lys Phe Ala Trp Pro Gln Tyr Leu Lys Thr Val Asp Gln His Gln Lys Ala Met Lys Pro Trp Thr Gln Pro Lys Thr Asn Ala Ile Pro Tyr Val Arg Tyr Leu >gp|S74171|S74171_1    α-S2 casein C-*capra hircus*
SEQUENCE:
                              (SEQ ID NO: 11)
Met Lys Phe Phe Ile Phe Thr Cys Leu Leu Ala Val Ala Leu Ala Lys His Lys Met Glu His Val Ser Ser Ser Glu Glu Pro Ile Asn Ile Phe Gln Glu Ile Tyr Lys Gln Glu Lys Asn Met Ala Ile His Pro Arg Lys Glu Lys Leu Cys Thr Thr Ser Cys Glu Glu Val Val Arg Asn Ala Asn Glu Glu Glu Tyr Ser Ile -continued Arg Ser Ser Ser Glu Glu Ser Ala Glu Val Ala Pro Glu Glu Ile Lys Ile Thr Val Asp Asp Lys His Tyr Gln Lys Ala Leu Asn Glu Ile Asn Gln Phe Tyr Gln Lys Phe Pro Gln Tyr Leu Gln Tyr Pro Tyr Gln Gly Pro Ile Val Leu Asn Pro Trp Asp Gln Val Lys Arg Asn Ala Gly Pro Phe Thr Pro Thr Val Asn Arg Glu Gln Leu Ser Thr Ser Glu Glu Asn Ser Lys Lys Thr Ile Asp Met Glu Ser Thr Glu Val Phe Thr Lys Lys Thr Lys Leu Thr Glu Glu Glu Lys Asn Arg Leu Asn Phe Leu Lys Lys Ile Ser Gln Tyr Tyr Gln Lys Phe Ala Trp Pro Gln Tyr Leu Lys Thr Val Asp Gln His Gln Lys Ala Met Lys Pro Trp Thr Gln Pro Lys Thr Asn Ala Ile Pro Tyr Val Arg Tyr Leu >pir|S39776|S39776            α-S2 casein form b
                                 precursor-rabbit
>gp|X76909|OCPAS2BCS_1    pre-α-S2b casein (AA -15 to
                                              167)
*Oryctolagus cuniculus*
SEQUENCE:
                              (SEQ ID NO: 12)
Met Lys Phe Phe Ile Phe Thr Cys Leu Leu Ala Val Ala Leu Ala Lys Pro Lys Ile Glu Gln Ser Ser Glu Glu Thr Ile Ala Val Ser Gln Glu Val Ser Pro Asn Leu Glu Asn Ile Cys Ser Thr Ala Cys Glu Glu Pro Ile Lys Asn Ile Asn Glu Val Glu Tyr Val Glu Val Pro Thr Glu Ile Lys Asp Gln Glu Phe Tyr Gln Lys Val Asn Leu Leu Gln Tyr Leu Gln Ala Leu Tyr Gln Tyr Pro Thr Val Met Asp Pro Trp Thr Arg Ala Glu Thr Lys Ala Ile Pro Phe Ile Arg Thr Met Gln Tyr Lys Gln Glu Lys Asp Ala Thr Lys His Thr Ser Gln Lys Thr Glu Leu Thr Glu Glu Lys Ala Phe Leu Lys Tyr Leu Asp Glu Met Lys Gln Tyr Tyr Gln Lys Phe Val Phe Pro Gln Tyr Leu Lys Asn Ala His His Phe Gln Lys Thr Met Asn Pro Trp Asn His Val Lys Thr Ile Ile Tyr Gln Val Pro Thr Ser Leu

[CAS2_SHEEP] α-S2 casein precursor-sheep
SEQUENCE:
(SEQ ID NO: 13)
Met Lys Phe Phe Ile Phe Thr Cys Leu Leu Ala Val Ala Leu Ala Lys His Lys Met Glu His Val Ser Ser Ser Glu Glu Pro Ile Asn Ile Ser Gln Glu Ile Tyr Lys Gln Glu Lys Asn Met Ala Ile His Pro Arg Lys Glu Lys Leu Cys Thr Thr Ser Cys Glu Glu Val Val Arg Asn Ala Asp Glu Glu Glu Tyr Ser Ile Arg Ser Ser Ser Glu Glu Ser Ala Glu Val Ala Pro Glu Glu Val Lys Ile Thr Val Asp Asp Lys His Tyr Gln Lys Ala Leu Asn Glu Ile Asn Gln Phe Tyr Gln Lys Phe Pro Gln Tyr Leu Gln Tyr Leu Tyr Gln Gly Pro Ile Val Leu Asn Pro Trp Asp Gln Val Lys Arg Asn Ala Gly Pro Phe Thr Pro Thr Val Asn Arg Glu Gln Leu Ser Thr Ser Glu Glu Asn Ser Lys Lys Thr Ile Asp Met Glu Ser Thr Glu Val Phe Thr Lys Lys Thr Lys Leu Thr Glu Glu Glu Lys Asn Arg Leu Asn Phe Leu Lys Lys Ile Ser Gln Tyr Tyr Gln Lys Phe Ala Trp Pro Gln Tyr Leu Lys Thr Val Asp Gln His Gln Lys Ala Met Lys Pro Trp Thr Gln Pro Lys Thr Asn Ala Ile Pro Tyr Val Arg Tyr Leu

[CAS2_PIG] α-S2 casein precursor-pig
SEQUENCE:
(SEQ ID NO: 14)
Met Lys Phe Phe Ile Phe Thr Cys Leu Leu Ala Val Ala Phe Ala Lys His Glu Met Glu His Val Ser Ser Ser Glu Glu Ser Ile Asn Ile Ser Gln Glu Lys Tyr Lys Gln Glu Lys Asn Val Ile Asn His Pro Ser Lys Glu Asp Ile Cys Ala Thr Ser Cys Glu Glu Ala Val Arg Asn Ile Lys Glu Val Glu Tyr Ala Ser Ser Ser Ser Ser Glu Glu Ser Val Asp Ile Pro Ala Glu Asn Val Lys Val Thr Val Glu Asp Lys His Tyr Leu Lys Gln Leu Glu Lys Ile Ser Gln Phe Tyr Gln Lys Phe Pro Gln Tyr Leu Gln Ala Leu Tyr Gln Ala Gln Ile Val Met Asn Pro Trp Asp Gln Thr Lys Thr Ser Ala Tyr Pro Phe Ile Pro Thr Val Ile Gln Ser Gly Glu Glu Leu Ser Thr Ser Glu Glu Pro Val Ser Ser Gln Glu Glu Asn Thr Lys Thr Val Asp Glu Ser Met Glu Glu Phe Thr Lys Lys Thr Glu Leu Thr Glu Glu Glu Lys Asn Arg Ile Lys Phe Leu Asn Lys Ile Lys Gln Tyr Tyr Gln Lys Phe Thr Trp Pro Gln Tyr Ile Lys Thr Val His Gln Lys Gln Lys Ala Met Lys Pro Trp Asn His Ile Lys Thr Asn Ser Tyr Gln Ile Ile Pro Asn Leu Arg Tyr Phe Furthermore, due to the similar nature of some amino acids it is possible to interchange some amino acids without affecting the functioning of the sequence. Accordingly leucine, isoleucine and valine may be interchanged. In addition tyrosine and phenylalanine may also be interchanged, as may arginine and lysine.

The invention will now be discussed in more detail. The invention preferably relates to α-S2 casein precursor fragments, and more preferably to the peptides referred to in WO 97/16460, for use as a cosmetic product, preferably in a cream or lotion, for reducing an aging effect in skin, such as wrinkles. The invention is preferably applicable to human skin, but may if desired be applied to other skin such as mammalian skin generally.

The invention also relates to the α-S2 casein precursor fragments mentioned above for use as a prophylactic agent or treatment agent for periodontal disease. This preferably relates to such diseases in humans, but may also apply to such diseases in mammalian gums generally if desired. The agent maybe in any suitable form, such as a topical agent (e.g. a toothpaste for cleaning the teeth and/or gums) or a chewing gum.

The peptide may be used as a pure product, or may conveniently be supplied as an enriched natural preparation from milk by following the protocols described in WO 97/16460 as far as (and including) the hydrophobic interaction chromatography step. Alternatively, cheese whey may be used in place of the acid (milk) whey.

The peptides may be used alone, or in combination with acceptable (in some cases pharmaceutically acceptable) additives and/or excipients useful for formulating topical compositions, toothpastes, or chewing gums. Additives for topical agents may include, for example, moisturising agents and/or other agents beneficial to the skin, such as all or any of vitamins A, C, D and E, that are used to beneficial effect to prevent/reverse the aging of skin.

Without being bound by theory, it is believed that the basis of the invention is that the peptides stimulate the growth of fibroblasts, the cells that underlie the surface of the skin and which are responsible for the synthesis of collagen, which in turn determines the thickness and smoothness of the skin. The peptides, as well as stimulating the growth of the fibroblasts, stimulate the synthesis and secretion of collagen. Furthermore, it is also believed that the peptides and derivatives used in the present invention also stimulate the growth of keratinocytes, which aid in the formation and regeneration of the skin surface.

The peptides used in the present invention appear to fulfill the equivalent role in bovine milk that EGF does in other species. The present inventors have surprisingly discovered that these peptides are effective as anti-periodontal disease agents and anti-aging agents and are more effective than known products. A further advantage of the peptides used in the present invention is that whilst they have an efficacy similar to, or are superior to, EGF they are regarded as being 'natural products' (being milk-derived) and because they have essentially no full protein content, they are not allergenic.

In a further aspect, the present invention provides use of a peptide, or a derivative of a peptide, in the manufacture of a medicament effective in alleviating or preventing an effect of aging in skin, wherein the peptide has an α-S2 casein fragment activity. Thus the peptide may be an α-S2 casein precursor fragment, as described in detail above, or can be a related molecule having a similar activity, such as a homologue.

In a related aspect, the present invention also provides use of a peptide, or a derivative of a peptide, in the manufacture of a medicament effective in alleviating or preventing periodontal disease, wherein the peptide has an α-S2 casein fragment activity. Thus, as in the related aspect, the peptide may be an α-S2 casein precursor fragment, as described in detail above, or can be a related molecule having a similar activity, such as a homologue.

Preferably the peptide used in the present invention is capable of stimulating the growth of fibroblasts. It is also preferred that the peptide is capable of stimulating fibroblasts to produce collagen. It is further preferred that the peptide is capable of stimulating growth in keratinocytes.

In a further aspect, the present invention provides a cosmetic method for alleviating or preventing an effect of aging in skin, which method comprises treating a subject with a peptide, wherein the peptide comprises an amino acid sequence present in an α-S2 casein precursor, said sequence comprising 3 or more amino acids, and not comprising at its N-terminus the N-terminal amino acid of the fill α-S2 casein precursor. The peptide is preferably a specific peptide as discussed in detail above, but alternatively may be an α-S2 casein precursor fragment, or a related molecule having a similar activity, such as a homologue.

In a still further aspect, the present invention provides a topical composition for alleviating or preventing an effect of aging in skin, comprising a peptide, or a derivative of a peptide, wherein the peptide comprises an amino acid sequence present in an α-S2 casein precursor, said sequence comprising 3 or more amino acids, and not comprising at its N-terminus the N-terminal amino acid of the full α-S2 casein precursor. The peptide is preferably a specific peptide as discussed in detail above, but alternatively may be an α-S2 casein precursor fragment, or a related molecule having a similar activity, such as a homologue.

In a related aspect, the invention provides a pharmaceutical composition for alleviating or preventing periodontal disease, comprising a peptide, or a derivative of a peptide, wherein the peptide comprises an amino acid sequence present in an α-S2 casein precursor, said sequence comprising 3 or more amino acids, and not comprising at its N-terminus the N-terminal amino acid of the full α-S2 casein precursor. Again, the peptide is preferably a specific peptide as discussed in detail above, but alternatively may be an α-S2 casein precursor fragment, or a related molecule having a similar activity, such as a homologue.

The invention will be further described by way of example only with reference to the following specific embodiments.

EXAMPLES

Example 1

Preparation of Standardised Natural Product from Cheese Whey

This procedure covers the methods for the collection, preparation and storage of Standardised Natural Product (SNP) from cheese whey. Typically, this procedure is used for small-scale preparation of SNP, such as for research and development purposes. However, the procedure can be scaled up as desired for commercial production according to known techniques.

Collection and Storage of Cheese Whey

Approximately 40 l of fresh clarified cheese whey was obtained from DewLay cheese manufacturing plant (Garstang, Lancashire). The whey was collected in clean containers and immediately transported to Pepsyn Central Manufacturing Facility (Liverpool).

Whey was either refrigerated for processing the following day or the whey was frozen at −20° C. in shallow 2 l containers until required.

Thawing of Cheese Whey

Frozen whey was thawed by placing a 2 l block of whey in a plastic bag and immersing it in hot running water. Thawing was completed in less than 10 mins and the temperature of the melting whey was maintained below 10° C.

Salting Out

The pH of the whey was adjusted to 3.0 using concentrated HCl. To each litre of whey, 220 g of $(NH_4)_2SO_4$ (BDH, AnalaR grade) was slowly added over a period of 30 mins whilst stirring. It was left to equilibrate for a further 1hr 30 mins without stirring, and then centrifuged at 9000 rpm for 40 mins using a SorvalIRC-5B centrifuge and associated GS-3 rotor (DuPont Instruments), which were pre-equilibrated to an operating temperature of between 4 and 10° C. To each litre of supernatant recovered, 130 g of $(NH_4)_2SO_4$ was added, and left to equilibrate and centrifuged as described above. The supernatant was discarded and the pellet was redissolved in distilled water (400 ml for each litre of whey started with). This was dialysed with visking tubing MWVCO 12,000 to 14,000 daltons (Medicell Int. Ltd, UK) against running tap water overnight and then with 20 mM sodium phosphate buffer at pH 6.0 for 7 hr with one change of buffer. The dialysed salt-cut was collected and either refrigerated for processing the following day or frozen (−20° C.) until required.

Cation Exchange Chromatography

Dialysed cheese whey salt-cut was run on cation-exchange chromatography, at 4° C. with a mobile phase of 20 mM sodium phosphate buffer, pH 6.0. Protein was eluted using a linear salt gradient of 100 to 700 mM NaCl provided by a gradient mixer (Pharmacia gradient mixer GM-1). The progress of the run was monitored at 280 nm using a UV monitor (Uvicord S II, Pharmacia).

A cation exchange column (Pharmacia X50series, 50 mm i.d.) was prepared with CM52 carboxythyl (Whatman) to a packed bed height of 15 cm. This was equilibrated with 500 of buffer solution. Dialysed cheese whey salt cut (400 ml) was loaded on the column at a flow rate of 2.5 ml/min and then washed overnight with 500 ml of 50 mM NaCl in buffer at a flow rate of about 0.5 ml/min. A 500 ml linear gradient of 100 to 700 mM NaCl in buffer was applied at a 2.0 ml/min and fractions were collected every 25 and numbered sequentially. The column was then washed with 300 ml of 2M NaCl in buffer. Collected fractions were tested for growth promoting activity., This was typically observed in fraction numbers 11 and 12 that contained lactoferrin, and also in the fractions just before and after these (see FIG. 1). Because lactoferrin gave a brown appearance to the fractions then this was used as a visual marker for activity. The mean estimated concentration of NaCl in each of the collected fractions is given in Table 1. All fractions were frozen until required for the next chromatographic step.

TABLE 1

Concentration of NaCl in each fraction from CM52 run.

| Fraction | Estimated NaCl (mM) | Fraction | Estimated NaCl (mM) |
|---|---|---|---|
| 5 | 115 | 15 | 415 |
| 6 | 145 | 16 | 445 |
| 7 | 175 | 17 | 475 |
| 8 | 205 | 18 | 505 |
| 9 | 235 | 19 | 535 |
| 10 | 265 | 20 | 565 |
| 11 | 295 | 21 | 595 |
| 12 | 325 | 22 | 625 |
| 13 | 355 | 23 | 655 |
| 14 | 385 | 24 | 685 |

N.B. Between the column inlet and outlet there was approximately 100 ml excluded volume. Therefore fraction 1 to 4 contained 50 mM NaCl from the wash buffer.

Hydrophobic Interaction Chromatography

Active fractions from cation exchange chromatography were run on hydrophobic interaction chromatography (HIC). This was performed at room temperature with a of 20 mM sodium phosphate buffer at pH 6.5. Protein was eluted using a linear salt gradient of 4 to 0 M NaCl provided by a gradient mixer (Pharmacia gradient mixer GM-1). The progress of the run was monitored at 280 nm using a UV monitor (Uvicord S II, Pharmacia).

A H-IC column (Pharmacia C series, 26 mm i.d) was prepared with Butyl Sepharose 4 Fast Flow (Pharmacia) to give a packed bed height of 15 cm. The column was equilibrated oversight with 250 ml of 4 M NaCl in buffer at a flow rate of 0.25 ml/min.

The active fractions from several cation exchange chromatography runs were pooled together to give between 100 and 200 ml of sample. The mean concentration of NaCl in this sample was calculated from the estimated concentrations of NaCl in the constituent fractions (Table 1). Solid NaCl was then slowly added to the sample to make it 3.7 M, and the pH was adjusted to 6.5. Sample was loaded on the column at 2.0 ml/min. A 500 ml eluting gradient of 4 M to 0 M NaCl was applied and fractions were collected every 25 ml and numbered sequentially. The column was then washed with 250 ml of buffer followed by 250 ml of water.

Collected fractions were tested for growth promoting activity. This was typically observed in fraction numbers 10 to 13, which were the fractions that eluted just before the brown lactoferrin fractions (see FIG. 2). Active fractions were pooled, extensively dialysed against distilled water and freeze-dried.

Example 2

Demonstration that SNP Increases Collagen Synthesis in Fibroblasts

Rama 27 rat mammary cells were grown to confluence, and their rate of synthesis of collagen was measured using the method of M. J. Warburton, S. A. Ferns, and P. S. Rudland, *Experimental Cell Research*, 137, 373-380 (1982). The rates of collagen synthesis as estimated by the incorporation of [3H] proline into hydroxyproline are set out in Table 2 below:

TABLE 2

Rates of collagen synthesis

| Concentration of SNP (mg/ml) | Cellular HO-proline (cpm) | Secreted HO-proline (cpm) |
|---|---|---|
| 0 | 53 | 54 |
| 0.2 | 271 | 233 |
| 0.4 | 232 | 327 |
| 0.6 | 321 | 663 |

Adding up to 0.6 mg/ml of SNP gives rise to an approximate 12-fold increase in the secretion of collagen—from 54 cpm to 663 cpm. This also gives rise to an approximate doubling in the ratio of synthesised collagen that is secreted to that which is retained in the cell—from 54:53 (1:1) to 663:321 (2:1).

Example 3

Demonstration of the Effect of SNP on the Growth of Keratinocytes

Human keratinocytes (HatKat) were grown in keratinocyte growth medium (TCS Cellworks Ltd.) until 20% confluence. Then, in the same medium, the keratinocytes were grown for three days with 0.5% foetal calf serum (FCS), at which point the cells were counted in a Coulter® counter. The cell numbers obtained are set out in Table 3 below.

TABLE 3

Cell numbers

| Conditions of growth | Number of cells |
|---|---|
| Medium with 0.5% FCS | 23,777 |
| Medium with 0.5% FCS + 10 ng/ml EGF | 29,356 |
| Medium with 0.5% FCS + 0.6 mg/ml SNP | 68,719 |

This shows that the presence of SNP gives rise to an approximate 3-fold increase in the growth of keratinocytes—from 23,777 to 68,719. This compares with a relatively modest increase with the use of 10 ng/ml EGF.

These results clearly demonstrate the collagen producing activity and growth promoting activity of the peptides used in the present invention.

The invention claimed is:

1. A medical or cosmetic method for alleviating or preventing an effect of aging in skin, said method comprising administering to a subject of an effective amount of a peptide wherein the peptide comprises an amino acid sequence present in an α-S2 casein precursor, said sequence comprising the last 3 amino acids of the C-terminal end of the α-S2 casein precursor, and not comprising at its N-terminus the N-terminal amino acid of the full α-S2 casein precursor, and wherein the peptide comprises an amino acid sequence selected from the following sequence:

```
                                              (SEQ ID NO: 2)
Lys Val Ile Pro Tyr Val Arg Tyr Leu;

(SEQ ID NO: 3)
Thr Lys Val Ile Pro Tyr Val Arg Tyr Leu;

(SEQ ID NO: 4)
Lys Thr Lys Val Ile Pro Tyr Val Arg Tyr Leu;

(SEQ ID NO: 5)
Pro Lys Thr Lys Val Ile Pro Tyr Val Arg Tyr Leu;
```

```
                                              (SEQ ID NO: 6)
Gln Pro Lys Thr Lys Val Ile Pro Tyr Val Arg
Tyr Leu;

(SEQ ID NO: 7)
Ala Met Lys Pro Trp Ile Gln Pro Lys Thr Lys
Val Ile Pro Tyr Val Arg Tyr Leu; and (SEQ ID NO: 8)
Pro Gln Tyr Leu Lys Thr Val Tyr Gln His Gln
Lys Ala Met Lys Pro Trp Ile Gln Pro Lys Thr Lys
Val Ile Pro Tyr Val Arg Tyr Leu.
```

2. A method according to claim 1, wherein the peptide comprise from 9-31 amino acids.

3. A method according to claim 1, wherein the effect of aging is wrinkling of the skin.

* * * * *